United States Patent [19]

Hardt

[11] 4,212,978

[45] * Jul. 15, 1980

[54] PROCESS FOR THE CATALYTIC PRODUCTION OF 2-SUBSTITUTED PYRIDINES

[75] Inventor: Peter Hardt, Visp, Switzerland

[73] Assignee: Lonzo Ltd., Gampel/Valais, Switzerland

[*] Notice: The portion of the term of this patent subsequent to Apr. 1, 1997, has been disclaimed.

[21] Appl. No.: 888,937

[22] Filed: Mar. 22, 1978

Related U.S. Application Data

[63] Continuation of Ser. No. 724,939, Sep. 20, 1976, abandoned.

[30] Foreign Application Priority Data

Sep. 18, 1975 [CH] Switzerland .................. 12139/75

[51] Int. Cl.² ........................................... C07D 213/08
[52] U.S. Cl. ................................. 546/253; 544/333; 546/250
[58] Field of Search ............ 260/290 P, 294.9, 296 D, 260/256.4 R, 295 R; 544/333; 546/250, 253

[56] References Cited

U.S. PATENT DOCUMENTS

| | | | |
|---|---|---|---|
| 3,829,429 | 8/1974 | Clement | 260/290 P |
| 4,006,149 | 2/1977 | Bonneman et al. | 260/290 P |

OTHER PUBLICATIONS

Wakatsuki et al., "Synthesis", 1976 (Jan.), No. 1, pp. 26–28.

*Primary Examiner*—Henry R. Jiles
*Assistant Examiner*—Bernard Dentz
*Attorney, Agent, or Firm*—Fisher, Christen & Sabol

[57] ABSTRACT

A process for the catalytic production of a 2-substituted pyridine which comprises reacting a corresponding cyano compound and acetylene in the presence of cobaltocene. A favorable conversion speed, a conversion of at least 90 percent, a good yield and a high selectivity are obtained.

8 Claims, No Drawings

PROCESS FOR THE CATALYTIC PRODUCTION OF 2-SUBSTITUTED PYRIDINES

This is a continuation application of application Ser. No. 724,939, filed on Sept. 20, 1976, now abandoned.

BACKGROUND OF THIS INVENTION

1. Field of This Invention

This invention relates to a process for the catalytic production of 2-substituted pyridines from the correspondingly substituted cyano compounds and acetylene using a cobalt catalyst.

2. Prior Art

It is known to produce 2-substituted pyridines from the corresponding carboxylic acid nitriles and acetylene in the presence of the catalyst cyclopentadienyl-triphenylphosphine-tetraphenyl cobaltacyclopentadiene or cyclopentadienyl-triphenylphosphine-cobalt diphenyl acetylene at yields of about 23 or 16 percent, respectively [Tetrahedron Letters No. 36, (1973) pp. 3383 and 3384].

Furthermore, methyl heptadienylcobalt-butadiene [Synthesis, (1974), p 575] and a number of other, partly simple cobalt compounds (U.S. Pat. No. 3,829,429) have been proposed as catalysts for these systems, The catalysts proposed or used hithertofore, however, provide uneconomical processes because of insufficient conversions and yields, as well as because of complicated partly multi-step production methods or insufficient thermal stability of the catalysts.

BROAD DESCRIPTION OF THIS INVENTION

An object of this invention is to provide a process for the catalytic production of 2-substituted pyridines from the correspondingly substituted cyano compounds and acetylene which has very high conversions, high selectivity, good conversion speeds and high yields. Other yields and advantages of this invention are set out herein or are obvious herefrom to one ordinarily skilled in the art.

The objects and advantages of this invention are achieved by the process of this invention.

This invention is based in part on the discovery that biscyclopentadienyl-cobalt (II) (i.e., cobaltocene) is eminently suitable for use as a catalylst for the production of 2-picoline and 2-substituted pyridines. This catalyst is easy to handle and, as is well known, can be produced easily from simple educts. A particular advantage in the use of cobaltocene as a catalyst consists in the fact that this catalyst can be used at high temperatures (above 80° C.). With such advantage quicker and more complete conversions of the cyano compounds are achieved, without promoting the known side reactions of the acetylene with itself to benzene and polymers.

This invention relates to a process for the production of 2-substituted pyridines from the corresponding cyano compounds and acetylene at conversions of at least 90 percent, good yields and high selectivity, characterized in that the reaction is carried out at a temperature above 80° C. in the presence of cobaltocene.

Cyano compounds which can be used as starting materials in the process of this invention are those which have the formula:

A—CN wherein A is alkyl having 1 to 8 carbon atoms, preferably 1 to 4 carbon atoms, cycloalkyl having 3 to 9 carbon atoms, alkenyl having 2 to 8 carbon atoms, aryl having 6 to 10 carbon atoms, cyanoaryl wherein the aryl moiety has 6 to 10 carbon atoms, pyridyl, pyrimidyl or

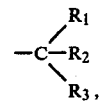

wherein $R_1$ is hydrogen or alkyl having 1 to 6 carbon atoms, preferably 1 to 4 carbon atoms, $R_2$ is hydrogen or alkyl having 1 to 6 carbon atoms, preferably 1 to 4 carbon atoms, and $R_3$ is cyanoalkyl wherein the alkyl moiety has 1 to 6 carbon atoms, preferably 1 to 4 carbon atoms, carbalkoxy alkyl wherein the alkyl moiety has 1 to 6 carbon atoms, preferably 1 to 4 carbon atoms, or aralkyl wherein the alkyl moiety preferably has 1 to 6 carbon atoms, and the aryl moiety has 6 to 10 carbon atoms, or wherein $R_1$ is hydrogen or alkyl having 1 to 6 carbon atoms, preferably 1 to 4 carbon atoms, $R_2$ is cyanoalkyl wherein the alkyl moiety has 1 to 6 carbon atoms, preferably 1 to 4 carbon atoms, carbalkoxyalkyl wherein the alkyl moiety has 1 to 6 carbon atoms, preferably 1 to 4 carbon atoms, or aralkyl wherein the alkyl moiety has 1 to 6 carbon atoms, preferably 1 to 4 carbon atoms, and the aryl moiety has 6 to 10 carbon atoms, and $R_3$ is cyanoalkyl wherein the alkyl moiety has 1 to 6 carbon atoms, preferably 1 to 4 carbon atoms, carbalkoxyalkyl wherein the alkyl moiety has 1 to 6 carbon atoms, preferably 1 to 4 carbon atoms, or aralkyl wherein the alkyl moiety has 1 to 6 carbon atoms, preferably 1 to 4 carbon atoms, and the aryl moiety has 6 to 10 carbon atoms.

Preferred starting cyano compounds are for example, acetonitrile, isobutyronitrile, acrylonitrile, crotononitrile, benzoic nitrile, benzylcyanide, adiponitrile, terephthalic acid dinitrile and cyanopyridine.

If a dicyano compound is used as the starting cyano compound, then, beside the 2-substituted pyridines carrying a cyano group on the substituent, the corresponding dipyridyl derivatives, such as, for example, from terephthaloyl dinitrile 2-(p-cyanophenyl)-pyridine/p-dipyridyl (2)-benzol or from adiponitrile δ-pyridyl (2)-valeronitrile/α,ω-dipyridyl (2)-butane, are obtained.

In order to carry out the process of this invention, the corresponding cyano compound and 0.1 to 1 mole percent of cobaltocene are saturated in a pressure vessel with 3 to 20 atm. of acetylene, preferably 6 to 12 atm., and are heated to 80° to 200° C. Reacted acetylene is repressed by charges or is taken continuously from a pressure flask. By suitable selection of the catalyst quantity, the pressure and the temperature within the stated limits, more than 20 moles of cyano compound can be reacted per mole of catalyst per hour. In the case of conversions up to 95 percent of the cyano compound, less than 10 mole percent of benzol is obtained, related to the pertinent 2-substituted pyridine.

Preferably, the reaction mixture is worked up by distillation. Unconverted cyano compound obtained from a first running, possibly also a mixture containing benzol, can again be used in further preparations of the reaction mixture.

Normally no solvent is required for carrying out the reaction, however for better heat flow, inert solvents, for example, benzol or the pyridine compound to be produced, can be used as diluents in case of the exothermal reaction.

The process can also be carried out continuously, for example, in a flow pipe.

This invention is described in more detail by the subsequent numbered examples. The yields relate to the cyano compound used. If not specifically mentioned, the conversions of the cyano compounds were better than 99 percent.

DETAILED DESCRIPTION OF THIS INVENTION

As used herein, an alkyl group (or moiety) of 1 to 4 carbon atoms can be, for example, methyl, ethyl, butyl, propyl, isopropyl, isobutyl, sec-butyl and t-butyl.

As used herein, an alkyl group (or moiety) of 1 to 6 carbon atoms can be, for example, methyl, ethyl, butyl, propyl, isopropyl isobutyl, sec-butyl, t-butyl, amyl, isoamyl, 2-pentyl, 3-pentyl, t-amyl, 3-methyl-2-butyl, 2-methyl-1-butyl, hexyl, 2-methyl-1-pentyl, 3-methyl-1-pentyl, isohexyl, 2-ethyl-1-butyl, 2-hexyl, 3-hexyl, 3-methyl-2-pentyl, 2,3-dimethyl-1-butyl, 4-methyl-2-pentyl, 2-methyl-3-pentyl, 2,2-dimethyl-3-butyl, 2-methyl-2-pentyl, 2,3-dimethyl-2-butyl and 3-methyl-3-pentyl.

As used herein, an alkyl group (or moiety) of 1 to 8 carbon atoms can be, for example, methyl, ethyl, butyl, propyl, isopropyl isobutyl, sec-butyl, t-butyl, amyl, isoamyl, 2-pentyl, 3-pentyl, t-amyl, 3-methyl-2-butyl, 2-methyl-1-butyl, hexyl, 2-methyl-1-pentyl, 3-methyl-1-pentyl, isohexyl, 2-ethyl-1-butyl, 2-hexyl, 3-hexyl, 3-methyl-2-pentyl, 2,3-dimethyl-1-butyl, 4-methyl-2-pentyl, 2-methyl-3-pentyl, 2,2-dimethyl-3-butyl, 2-methyl-2-pentyl, 2,3-dimethyl-2-butyl, 3-methyl-3-pentyl, heptyl, 2,4-dimethyl-3-pentyl, 2,4-dimethyl-1-pentyl, 4-methyl-1-hexyl, 2,3,3-trimethyl-2-butyl, octyl and 2-octyl.

As used herein, an aryl group (moiety) having 6 to 10 carbon atoms can be for example, phenyl, 1-naphthyl and 2-naphthyl.

As used herein, a cycloalkyl group moiety having 3 to 9 carbon atoms can be, for example, cyclobutyl, cycloheptyl, cyclohexyl, 1,3-dimethyl cyclohexyl, 1,4-dimethyl cyclohexyl, isopropyl cyclohexyl, 1,3,5-trimethyl cyclohexyl, cyclopentyl and methyl cyclohexyl.

As used herein, an alkenyl group (moiety), $C_nH_{2n-1}$, having 2 to 8 carbon atoms can be, for example, propenyl, ethenyl, pentenyl, 1-butenyl, 3-butenyl, 2-butenyl, hexenyl, octenyl and heptenyl.

As used herein, all parts, ratios, percentages and ratios are on a weight basis unless otherwise stated herein or otherwise obvious herefrom to one ordinarily skilled in the art.

EXAMPLE 1

1.1 gm. of cobaltocene (0.006 M) is dissolved under nitrogen in 38.8 gm. of acetonitrile (0.946 M) and are stirred in a 1-liter autoclave at 12 atm. acetylene pressure and 175° C. for 7.5 hours. After this is allowed to cool and relax, it is distilled in a simple Vigreux column. From 93 gm. of raw product, and after first runnings from acetonitrile and benzol, 67.6 gm. of 2-picoline having a purity of 99.5 percent was obtained, corresponding to a yield of 76.4 percent pure product.

EXAMPLE 2

A solution of 0.2 gm. (0.001 M) of cobaltocene in 39.5 gm. (0.963 M) of acetonitrile was saturated at room temperature in a stirring autoclave with 11.5 atm. of acetylene and heated to 180° C. within 1 hour. After the pressure had dropped after 2 hours from 26 to 8 atm, the reaction was allowed to continue for 4 hours at 11.5 atm. of acetylene pressure. After the reaction mixture was allowed to cool and the pessure dropped to atmospheric, the raw product was distilled. 6 gm. of a mixture of 81.6 percent benzol and 18.2 percent acetonitrile and 73.9 gm. of 2-picoline was obtained. The 2-picoline had a purity of 99.6 percent. That corresponds to a conversion of 97.2 percent acetonitrile, a yield of 82.2 percent 2-picoline and the formation of 7.9 mole percent benzol.

EXAMPLE 3

Analogously to Example 1, 17.7 gm. of acrylonitrile (0.333 M) and 0.5 gm. (0.003 M) of cobaltocene in 45.1 gm. of benzol with 12 atm. of acetylene were reacted at 120° C. for 60 min. and subsequently vacuum distilled. 12.4 gm of 2-vinylpyridine were obtained with a purity of 97.1 percent, which corresponds to a yield of 34.4 percent. In addition, 3.1 gm of acrylonitrile were recaptured, corresponding to a conversion of about 83 percent.

EXAMPLE 4

Analogously to Example 1, 43.7 gm. of benzylcyanide (0.373 M) with 0.5 gm. of cobaltocene (0.003 M) were saturated at 12 atm with acetylene and were heated for 2 hrs. to and at 175° C. After cooling, the reaction mixture was relaxed from 5.5 atm. to standard pressure, and distilled. 43.3 gm. of 2-benzylpyridine with a purtiy of 98.8 percent, corresponding to a yield of 68 percent, was obtained.

EXAMPLE 5

3.6 atm. of acetylene was pressed onto a solution of 2.8 gm. (0.015 M) of cobaltocene in 115.3 gm. (1.67 M) of 1-butyronitrile in a 1-liter stirring autoclave. Subsequently, the reaction mixture was heated in 60 minutes to 170° C. and was stirred for 5 hours with continuous addition of acetylene from an 11.5 atm pressure bottle. By flash distillation, 179.4 gm. of a mixture of 5.7 percent benzol, 2.1 percent i-butyronitrile and 91.1 percent of 2-isopropyl pyridine was obtained. 96.7 percent of converted isobutyronitrile, 81 percent yield and a formation of 9.7 mole percent of benzol, related to isopropylpyridine, correspond to the distilled product.

EXAMPLE 6

A solution of 25.0 gm of 3-cyanopyridine (0.24 m) and 0.4 gm. of cobaltocene (0.002 M) in 25 ml of benzol was heated in a stirring autoclave, after 12 atm of acetylene had been inserted (pressed on) for 3 hrs. to and at 180° C. 27 gm. of 99.2 percent 2,3'-dipyridile was obtained by distillation correspondng to a yield of 71.4 percent.

EXAMPLE 7

Analogously to Example 1, 49.9 gm. of benzonitrile (0.484 M) and 0.8 gm. of cobaltocene (0.004 M) were heated with 12 atm of acetylene to and at 160° C. 59 gm. of 99.6 percent 2-phenylpyridine was obtained, which corresponds to 78.3 percent of theory.

EXAMPLE 8

Analogously to Example 5, 0.7 gm. of cobaltocene in 36.6 gm. of crotonic acid nitrile at 165° C. for 6 hours was treated with acetylene. After this the reaction mixture was allowed to cool, relaxed to atmospheric pressure and flash distilled in a vacuum. 48.5 gm. of a colorless condensate were obtained, which according to gas chromatography contained 5.4 percent benzol, 6.4 percent crotonic acid nitrile and 70.1 percent 2-propenylpyridine as the cis-trans isomer mixture. Conversion was about 92 percent; the yield was about 52.3 percent.

EXAMPLE 9

0.4 gm. of cobaltocene was dissolved in 20.8 gm. of benzol and 16.0 gm. of methacrylonitrile. The mixture was placed into an autoclave, was saturated with 12 atm of acetylene at 25° C. and was heated to and at 150° C. for 6 hours. As in Example 8, 39.7 gm. of a condensate was obtained, which beside benzol contained 18.6 percent methacrylonitrile and 24.6 percent 2-isopropenyl pyridine. Conversion was about 54 percent; yield was about 34.4 percent.

EXAMPLE 10

0.6 gm. of cobaltocene in 43 gm. of benzol was treated in an autoclave (while excluding air) with 39.8 gm. of 4-cyanopyridine. The mixture was saturated with 12 atm. of acetylene and heated to 180° C. After 2 hours the autoclave was cooled. Again 12 atm. acetylene was pressed on, and the mixture was heated another 4 hours to and at 180° C. After allowing the reaction mixture to cool and unstress (depressurized), 41.5 gm. of a fraction was obtained by distillation (Kp 120°–130° C./0.02 torr). The fraction contained 9.2 percent 4-cyanopyridine and 90.7 percent 2,4'-dipyridyl. 2,4'-dipyridyl was isolated from ligroin by recrystallization of this fraction. The conversion was 90.4 percent; the yield was 63.0 percent.

EXAMPLE 11

As in Example 10, 27.1 gm. of benzol, 0.5 gm. of cobaltocene and 30.0 gm. of terephthalic acid nitrile was reacted with acetylene. After distilling off the benzol by vacuum distillation, 39.5 gm. of a sublimate having about 9 percent terephthalic acid nitrile, 70 percent 4-(2-pyridyl)-benzoic nitrile and 21 percent 1,4-di-(2-pyridyl)-benzol were obtained. The compounds were isolated using fractionating sublimation and recrystallization from acetone.

EXAMPLE 12

37.9 gm. of adipic acid dinitrile and 0.7 gm. of cobaltocene were saturated in the autoclave at 20° C. at a pressure of 12 atm and were heated to 180° C. This was cooled down to 30° C. after 60 minutes and acetylene was re-pressed (pressured). After another 3 hours, the reaction mixture was cooled and expanded at 180° C. The fractionating distillation of the reaction product resulted in 4.3 gm. of adipic acid nitrile, 28.8 gm. of ω-(2-pyridyl)-valeronitrile and 14.7 gm. of α-ω-di-(2-pyridyl)-butane.

What is claimed is:
1. A process for the catalytic production of a 2-substituted pyridine which comprises reacting a cyano compound and acetylene in the presence of cobaltocene, which is a catalyst, said reaction being conducted at a pressure between 3 and 20 atmospheres of acetylene, and said cobaltocene not being converted to a different valence state during the process, whereby said cyano compound has the formula:

A—CN wherein A is alkyl having 1 to 8 carbons, cycloalkyl having 3 to 9 carbon atoms, alkenyl having 2 to 8 carbon atoms, aryl having 6 to 10 carbon atoms, cyanoaryl wherein the aryl moiety has 6 to 10 carbon atoms, pyridyl, pyrimidyl or

wherein $R_1$ is hydrogen or alkyl having 1 to 6 carbon atoms, $R_2$ is hydrogen or alkyl having 1 to 6 carbon atoms, and $R_3$ is cyanoalkyl wherein the alkyl moiety has 1 to 6 carbon atoms, carbalkoxy alkyl wherein the alkyl moiety has 1 to 6 carbon atoms, or aralkyl wherein the alkyl moiety has 1 to 6 carbon atoms and the aryl moiety has 6 to 10 carbon atoms, or wherein $R_1$ is hydrogen or alkyl having 1 to 6 carbon atoms, $R_2$ is cyanoalkyl wherein the alkyl moiety has 1 to 6 carbon atoms, carbalkoxyalkyl wherein the alkyl moiety has 1 to 6 carbon atoms, or aralkyl wherein the alkyl moiety has 1 to 6 carbon atoms and the aryl moiety has 6 to 10 carbon atoms, and $R_3$ is cyanoalkyl wherein the alkyl moiety has 1 to 6 carbon atoms, carbalkoxyalkyl wherein the alkyl moiety has 1 to 6 carbon atoms, or aralkyl wherein the arlkyl moiety has 1 to 6 carbon atoms and the aryl moiety has 6 to 10 carbon atoms, whereby said 2-substituted pyridine is obtained.

2. A process as claimed in claim 1 wherein said cyano compound is acetonitrile, isobutyronitrile, acrylonitrile, crotononitrile, adiponitrile, benzonitrile, benzylcyanide, terephthalic acid nitrile and cyanopyridine.

3. A process as claimed in claim 1 wherein said cobaltocene is used in an amount between 0.1 and 1 mole percent, related to said cyano compound.

4. A process as claimed in claim 3 wherein said reaction is conducted at a temperature between 80° and 200° C.

5. A process as claimed in claim 1 wherein said reaction is conducted at temperatures above 80° C.

6. A process as claimed in claim 1 wherein an inert solvent is present in the reaction mixture.

7. A process as claimed in claim 1 wherein A in the formula A—CN is alkyl having 1 to 4 carbon atoms.

8. A process as claimed in claim 1 wherein A is

wherein $R_1$ is alkyl having 1 to 4 carbon atoms.

* * * * *

UNITED STATES PATENT OFFICE
CERTIFICATE OF CORRECTION

Patent No. 4,212,978     Dated July 15, 1980

Inventor(s) Peter Hardt

It is certified that error appears in the above-identified patent and that said Letters Patent are hereby corrected as shown below:

In the heading, item [73], cancel "Lonzo Ltd." and insert therefor --Lonza Ltd.--.

Signed and Sealed this

Twenty-eighth Day of October 1980

[SEAL]

Attest:

Attesting Officer

SIDNEY A. DIAMOND

Commissioner of Patents and Trademarks